(12) United States Patent
Morimoto et al.

(10) Patent No.: US 11,298,273 B2
(45) Date of Patent: Apr. 12, 2022

(54) WEARABLE ARTICLE HAVING ELASTIC BELT

(71) Applicant: The Procter & Gamble Company, Cincinnati, OH (US)

(72) Inventors: Koichi Morimoto, Beijing (CN); Chunmin Cheng, Beijing (CN); Masaharu Nishikawa, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1179 days.

(21) Appl. No.: 15/423,856

(22) Filed: Feb. 3, 2017

(65) Prior Publication Data

US 2018/0221218 A1 Aug. 9, 2018

(51) Int. Cl.
*A61F 13/496* (2006.01)
*A61F 13/49* (2006.01)

(52) U.S. Cl.
CPC ...... *A61F 13/496* (2013.01); *A61F 13/49011* (2013.01); *A61F 13/49061* (2013.01)

(58) Field of Classification Search
CPC ............ A61F 13/49011; A61F 13/4902; A61F 13/49061; A61F 13/496; A61F 13/4963;

(Continued)

(56) References Cited

U.S. PATENT DOCUMENTS 5,196,000 A 3/1993 Clear et al.
5,749,865 A * 5/1998 Yamamoto ............ A61F 13/496
604/385.29

(Continued)

FOREIGN PATENT DOCUMENTS

CN 100482190 C 4/2009
EP 2659870 11/2013

(Continued)

OTHER PUBLICATIONS

Merries Pants L size product disclosure at https://web.kao.com/sg/merries/products/pants_l_xl/ accessed Dec. 3, 2019 (Year: 2019).*

(Continued)

*Primary Examiner* — Kathryn E Ditmer
(74) *Attorney, Agent, or Firm* — Charles R. Matson; Richard L. Alexander (57) ABSTRACT

Disclosed is a wearable article continuous in a longitudinal direction and a transverse direction, comprising a main body and an elastic belt comprising a front belt and a back belt, the main body being continuous with the front belt and the back belt, and the transverse edges of the front belt and the back belt are joined by a seam to form a waist opening and two leg openings, wherein each of the front belt and back belt are formed by an inner sheet, an outer sheet, and a plurality of elastic bodies sandwiched therebetween, wherein at least some of the elastic bodies run in the transverse direction substantially parallel to each other, wherein according to the Material Circumference Measurement and the Whole Article Force Measurement herein, the Belt Utilization is no less than 92%, and the Fit Circumference Force is greater than 2.0N.

18 Claims, 6 Drawing Sheets

(58) Field of Classification Search
CPC .. A61F 2013/49025; A61F 2013/49026; A61F 2013/49028
See application file for complete search history.

(56) References Cited

U.S. PATENT DOCUMENTS

| | | | |
|---|---|---|---|
| 7,569,039 B2 | 8/2009 | Matsuda et al. | |
| 8,206,365 B2 | 6/2012 | Norrby | |
| 9,358,162 B2 | 6/2016 | Kuwano et al. | |
| 10,085,894 B2 | 10/2018 | LaVon et al. | |
| 2003/0181883 A1 | 9/2003 | Olson et al. | |
| 2005/0107764 A1* | 5/2005 | Matsuda | A61F 13/49011 604/396 |
| 2005/0126689 A1 | 6/2005 | Thorson et al. | |
| 2006/0025746 A1* | 2/2006 | Sasaki | A61F 13/15203 604/386 |
| 2008/0108964 A1 | 5/2008 | Edwall | |
| 2011/0106039 A1* | 5/2011 | Saito | A61F 13/49011 604/385.3 |
| 2012/0157955 A1 | 6/2012 | Ashton et al. | |
| 2012/0289921 A1* | 11/2012 | Hashino | A61F 13/49406 604/385.3 |
| 2013/0041340 A1* | 2/2013 | Kawakami | A61F 13/49009 604/385.29 |
| 2013/0079742 A1* | 3/2013 | Kuwano | A61F 13/49011 604/385.3 |
| 2013/0211363 A1* | 8/2013 | LaVon | A61F 13/49012 604/385.3 |
| 2013/0281955 A1* | 10/2013 | Kobayashi | A61F 13/15699 604/385.3 |
| 2014/0358110 A1* | 12/2014 | Takahashi | A61F 13/496 604/385.29 |
| 2014/0378932 A1* | 12/2014 | Seitz | A61F 13/55105 604/385.3 |
| 2015/0230996 A1 | 8/2015 | Lavon et al. | |
| 2017/0105886 A1* | 4/2017 | Shirai | A61F 13/49011 |
| 2018/0303681 A1* | 10/2018 | Back | A61F 13/49011 |
| 2018/0333311 A1* | 11/2018 | Maki | A61F 13/49 |

FOREIGN PATENT DOCUMENTS

| | | | | |
|---|---|---|---|---|
| EP | 2659870 A1 * | 11/2013 | | A61F 13/496 |
| JP | 2007195647 | 8/2007 | | |
| JP | 2012135519 A | 7/2012 | | |
| JP | 2019502497 A | 1/2019 | | |
| WO | WO-2006017718 A1 * | 2/2006 | | A61F 13/15804 |
| WO | WO 2006017718 A1 | 2/2006 | | |
| WO | WO-2013005423 A1 * | 1/2013 | | A61F 13/496 |

OTHER PUBLICATIONS

Merries Pants product review at https://theblissfulbloom.com/2017/09/20/merries-diapers-no-1-baby-diaper-in-japan-receives-a-warm-welcome-from-baby-tash/ (Year: 2017).*

International Search Report and Written Opinion, PCT/CN2016/073256, dated Mar. 26, 2018.

PCT Search Report and Written Opinion for PCT/CN2016/073256 dated Nov. 7, 2016, 6 pages.

* cited by examiner

WEARABLE ARTICLE HAVING ELASTIC BELT

CROSS REFERENCE TO RELATED APPLICATION

This application is a continuation of, and claims priority under 35 U.S.C. § 120 to, Application No. PCT/CN2016/073256, filed on Feb. 3, 2016, of which is herein incorporated by reference in its entirety.

FIELD OF THE INVENTION

The present invention relates to wearable articles having an elastic belt of particular dimension and force profiles.

BACKGROUND OF THE INVENTION

Infants and other incontinent individuals wear wearable articles such as diapers to receive and contain urine and other body exudates. Pull-on wearable articles, or pant-type wearable articles, are those which are donned by inserting the wearer's legs into the leg openings and sliding the article up into position about the lower torso. Pant-type absorbent articles have become popular for use on children who are able to walk and often who are toilet training, as well as for younger children who become more active in movement such that application of taped-type absorbent articles tends to be more difficult.

Many pant-type wearable articles use elastic elements secured in an elastically contractible condition in the waist and/or leg openings. Typically, in order to insure full elastic fit about the leg and the waist such as is provided with durable undergarments, the leg openings and waist opening are encircled at least in part with elasticized elements positioned along the periphery of the respective opening.

Pant-type wearable articles having a main body to cover the crotch region of the wearer and a separate elastic belt defining the waist opening and leg opening are known in the art, such as described in PCT Publication WO 2006/017718A. Such pant-type wearable articles may be referred to as belt-type pants. On the other hand, certain pant-type wearable articles are configured such that the outer cover of the wearable body completely covers the entirety of the garment-facing surface of the article. Such pant-type wearable articles may be referred to as uni-body pants. Whether the uni-body type or the belt-type, there is a desire to provide pant-type wearable articles to be easily stretched open upon application and have a soft fit to the skin to avoid red markings during wear, while having enough force to prevent the article from sagging after loading. Meanwhile, there is a desire to provide pant-type wearable articles in an economical manner, for example, by using as less material as possible.

Based on the foregoing, there is a need for a pant-type wearable article having balanced performance such as ease of application, fit, comfort during wear, prevention of sagging, and prevention of leakage. There is further a need for providing such a wearable article in an economical manner.

SUMMARY OF THE INVENTION

The present invention is directed to a wearable article continuous in a longitudinal direction and a transverse direction, comprising a main body and an elastic belt comprising a front belt and a back belt, the main body being continuous with the front belt and the back belt, and the transverse edges of the front belt and the back belt are joined by a seam to form a waist opening and two leg openings, wherein each of the front belt and back belt are formed by an inner sheet, an outer sheet, and a plurality of elastic bodies sandwiched therebetween, wherein at least some of the elastic bodies run in the transverse direction substantially parallel to each other, wherein according to the Material Circumference Measurement and the Whole Article Force Measurement herein, the Belt Utilization is no less than 92%, and the Fit Circumference Force is greater than 2.0N.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings and which like designations are used to designate substantially identical elements, and in which:

DEFINITIONS

As used herein, the following terms shall have the meaning specified thereafter:

"Wearable article" refers to articles of wear which may be in the form of pants, taped diapers, incontinent briefs, feminine hygiene garments, and the like. The "wearable article" may be so configured to also absorb and contain various exudates such as urine, feces, and menses discharged from the body. The "wearable article" may serve as an outer cover adaptable to be joined with a separable disposable absorbent insert for providing absorbent and containment function, such as those disclosed in PCT publication WO 2011/087503A.

"Pant" refers to disposable absorbent articles having a pre-formed waist and leg openings. A pant may be donned by inserting a wearer's legs into the leg openings and sliding the pant into position about the wearer's lower torso. Pants are also commonly referred to as "closed diapers", "prefastened diapers", "pull-on diapers", "training pants" and "diaper-pants." "Longitudinal" refers to a direction running substantially perpendicular from a waist edge to an opposing waist edge of the article and generally parallel to the maximum linear dimension of the article.

"Transverse" refers to a direction perpendicular to the longitudinal direction.

"Body-facing" and "garment-facing" refer respectively to the relative location of an element or a surface of an element or group of elements. "Body-facing" implies the element or surface is nearer to the wearer during wear than some other element or surface. "Garment-facing" implies the element or surface is more remote from the wearer during wear than some other element or surface (i.e., element or surface is proximate to the wearer's garments that may be worn over the disposable absorbent article).

"Disposed" refers to an element being located in a particular place or position.

"Joined" refers to configurations whereby an element is directly secured to another element by affixing the element directly to the other element and to configurations whereby an element is indirectly secured to another element by affixing the element to intermediate member(s) which in turn are affixed to the other element.

"Extendibility" and "extensible" mean that the width or length of the component in a relaxed state can be extended or increased.

"Elasticated" and "elasticized" mean that a component comprises at least a portion made of elastic material.

"Elongatable material," "extensible material," or "stretchable material" are used interchangeably and refer to a material that, upon application of a biasing force, can stretch to an elongated length of at least about 110% of its relaxed, original length (i.e. can stretch to 10 percent more than its original length), without rupture or breakage, and upon release of the applied force, shows little recovery, less than about 20% of its elongation without complete rupture or breakage as measured by EDANA method 20.2-89. In the event such an elongatable material recovers at least 40% of its elongation upon release of the applied force, the elongatable material will be considered to be "elastic" or "elastomeric." For example, an elastic material that has an initial length of 100 mm can extend at least to 150 mm, and upon removal of the force retracts to a length of at least 130 mm (i.e., exhibiting a 40% recovery). In the event the material recovers less than 40% of its elongation upon release of the applied force, the elongatable material will be considered to be "substantially non-elastic" or "substantially non-elastomeric". For example, an elongatable material that has an initial length of 100 mm can extend at least to 150 mm, and upon removal of the force retracts to a length of at least 145 mm (i.e., exhibiting a 10% recovery).

DETAILED DESCRIPTION OF THE INVENTION

Figure 1:
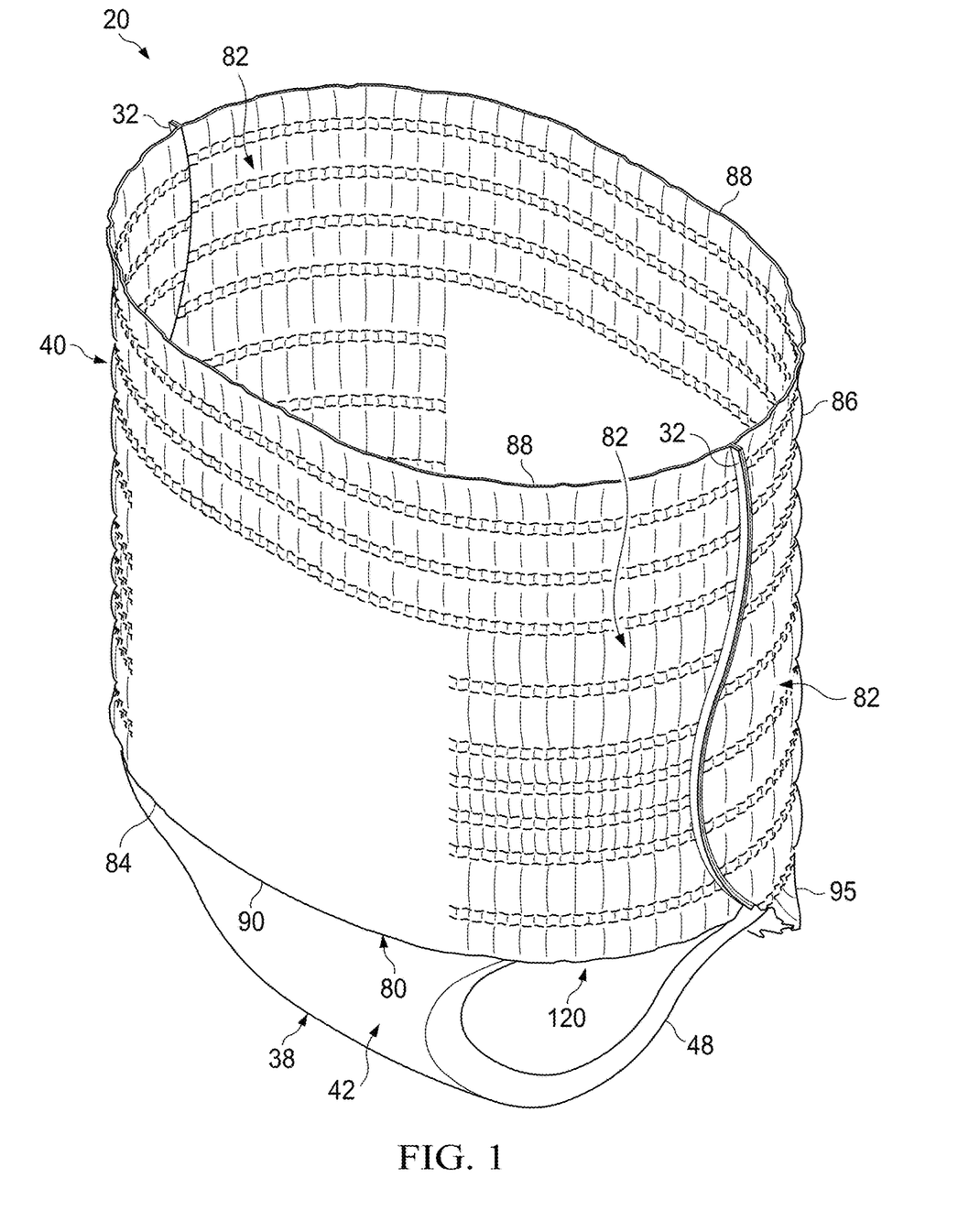
FIG. 1 is a perspective view of one embodiment of a wearable article of the present invention.
Figure 2:
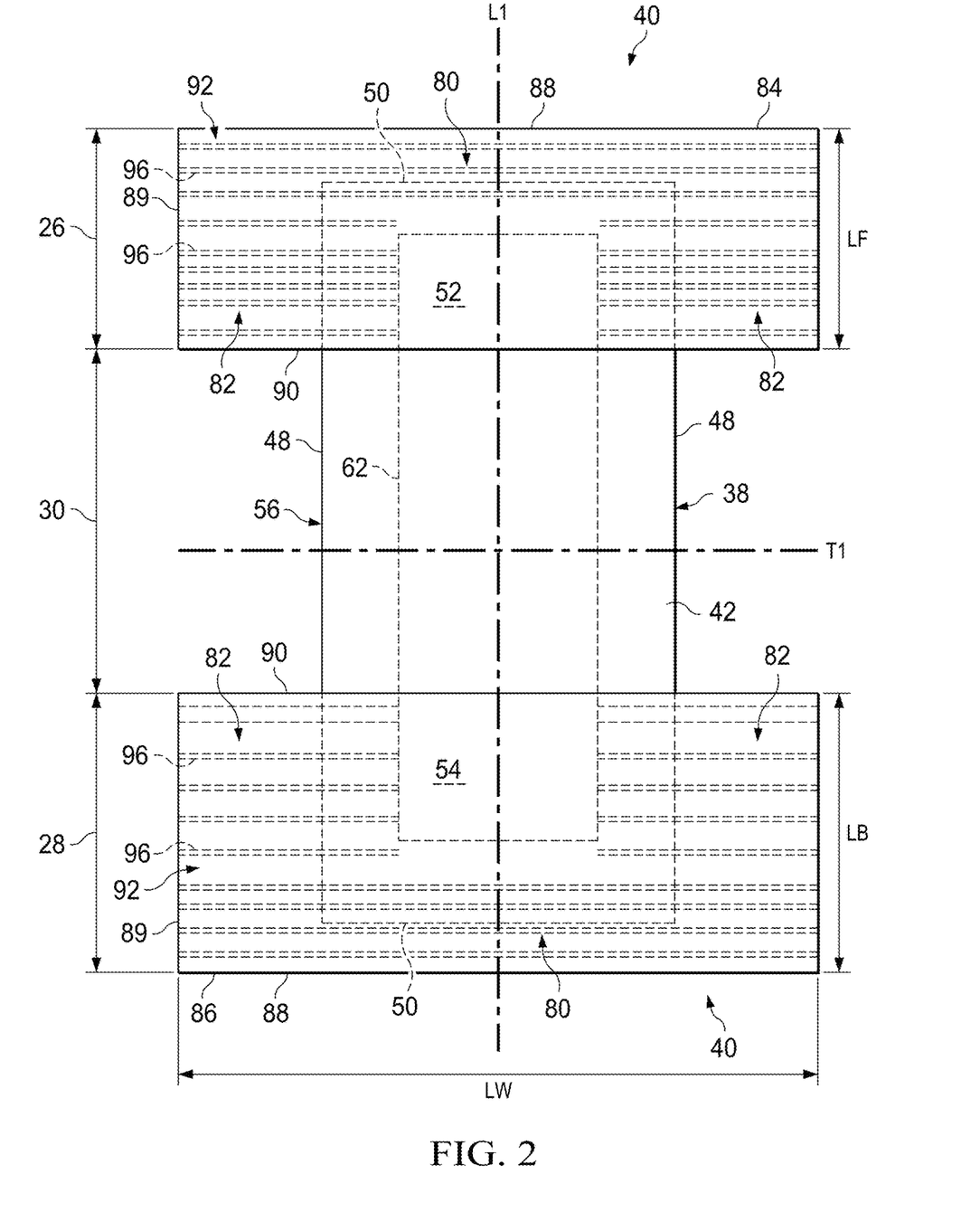
FIG. 2 is a schematic plan view of one embodiment of a wearable article of the present invention with the seams unjoined and removed, and in a flat uncontracted condition showing the garment facing surface.

FIG. 1 is a perspective view of an embodiment of the wearable article 20 of the present invention and FIG. 2 is a schematic plan view of the same article with the seams unjoined and in its flat uncontracted condition showing the garment-facing surface. The wearable article 20 has a longitudinal centerline L1 which also serves as the longitudinal axis, and a transverse centerline T1 which also serves as the transverse axis. The wearable article 20 of the present invention has a skin-facing surface, a garment-facing surface, a front region 26, a back region 28, a crotch region 30, and seams 32 which join the front region 26 and the back region 28 to form two leg openings and a waist opening. The wearable article 20 comprises a main body 38 to cover the crotch region 30 of the wearer, a front belt 84 and a back belt 86 to cover the front region 26 and back region 28, the front and back belts 84, 86 and the main body being continuous. The front and back belts 84, 86 may jointly form a ring-like elastic belt 40 (hereinafter may be referred to as "waist belt") extending transversely defining the waist opening. The transverse edges of the front belt 84 and the back belt 86 are joined by seams 32 to form a waist opening and two leg openings. When the front and back belts 84, 86 form a ring-like elastic belt 40, the front and back belts 84, 86 and the main body 38 jointly define the leg openings.

The main body 38 may contain an absorbent core 62 for absorbing and containing body exudates disposed on the main body 38. In the embodiment shown in FIG. 2, the main body 38 has a generally rectangular shape, left and right longitudinally extending side edges 48 (hereinafter may be referred to as "side edge") and front and back transversely extending end edges 50 (hereinafter may be referred to as "end edge"). The main body 38 also has a front waist panel 52 positioned in the front region 26 of the wearable article 20, a back waist panel 54 positioned in the back region 28, and a crotch panel 56 between the front and back waist panels 52, 54 in the crotch region 30. The center of the front belt 84 may be joined to a front waist panel 52 of the main body 38, the center of the back belt 86 is joined to a back waist panel 54 of the main body 38, the front and back belt 84, 86 each having a left side panel and a right side panel 82 where the main body 38 does not overlap.

Referring to FIGS. 1 and 2, the elastic belt 40 formed at least partly by the front belt 84 and back belt 86 acts to dynamically create fitment forces and to distribute the forces dynamically generated during wear. Herein, the term "proximal" is used to indicate the position of a "proximal" portion being closer relative to the longitudinal center of the article, also closer relative to the crotch panel 56 of the main body 38 than the position of a "distal" portion. Therefore, the proximal edge 90 is located closer than the distal edge 88 relative to the crotch panel 56 of the main body 38. The front and back belts 84, 86 may be joined with each other only at the side edges 89 at the seams 32 to form a wearable article having a waist opening and two leg openings. Each leg opening may be provided with elasticity around the perimeter of the leg opening by the combination of elasticity from the front belt 84, the back belt 86, and any from the main body 38. For example, the front leg opening region 120 is disposed adjacent the leg opening along the proximal edge 90 of the left and right side panels 82 of the front belt 84.

The front and back belts 84, 86 may be continuous or discontinuous with one another in the crotch region 30. When the front and back belts 84, 86 are discontinuous, there is no material that covers the entirety of either the wearer-facing surface or garment-facing surface of the article. The front central panel 80 may partly overlap with the front waist panel 52 of the main body 38. The back central panel 80 may partly overlap with the back waist panel 54 of the main body 38. However, the central panels 80 may not extend into the crotch panel 56 of the main body 38 and not be disposed in the crotch panel 56. In the embodiment shown in FIG. 2, the central panels 80 partly overlap with and are joined to the front waist panel 52 and the back waist panel 54, respectively.

The front belt 84 and back belt 86 may each comprise an inner sheet 94, an outer sheet 92, (hereinafter also collectively "belt sheets") and a plurality of elastic bodies 96 sandwiched therebetween wherein at least some of the elastic bodies running in the transverse direction substantially parallel to each other, and configured to impart elasticity in the front and back regions 26, 28. Referring to FIG. 2, all of the elastic bodies sandwiched between the inner sheet and the outer sheet may run in the transverse direction substantially parallel to each other. (The inner sheet 94 is not shown.) Such an article may be economically made.

The effective transverse width LW of the back belt 86 in the uncontracted condition may be the same as the transverse width of the front belt 84 of the same condition. By "effective transverse width", what is meant is the width available for forming the wearer-facing surface of the article. Each of the proximal edges 90 and the distal edges 88 of the front belt 84 and the back belt 86 may be substantially parallel, as in FIG. 2.

The longitudinal length LB of the back belt 86 between the back distal edge 88 and the back proximal edge 90 along its entire width LW of the back belt 86 may be approximately the same as the longitudinal length LF of the front belt 84 between the front distal edge 88 and the front proximal edge 90. In such embodiment, the seams 32 close the front and back belt 84, 86 side edges 89 of the same length for forming the article. Such an article may be economically made.

Figure 3:
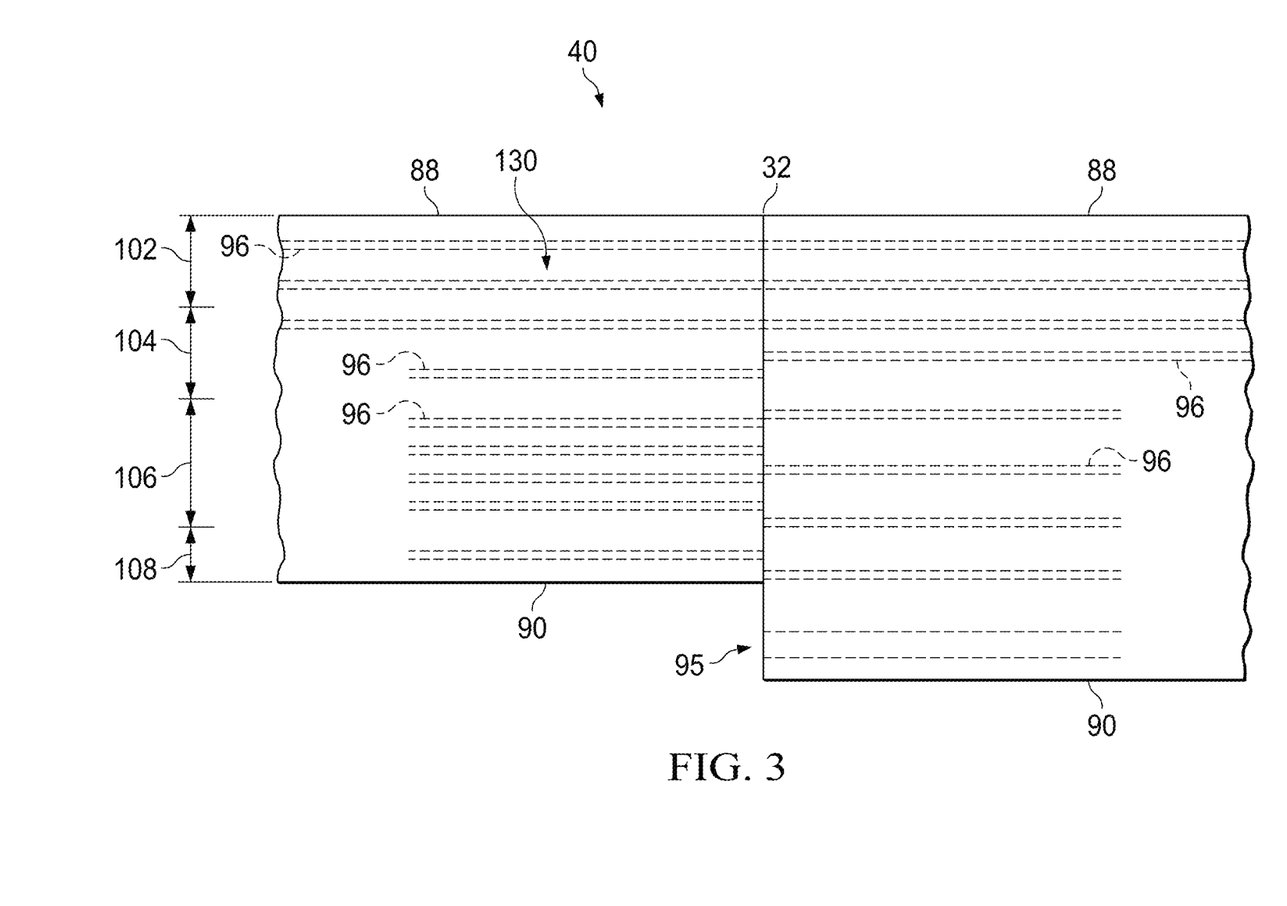
FIG. 3 is a schematic side plan view of one embodiment of a wearable article of the present invention in a flat uncontracted condition showing the garment facing surface.

The back belt 86 may have a greater longitudinal length LB between the back distal edge 88 and the back proximal edge 90 along its entire width LW of the back belt 86 in the transverse direction than the longitudinal length LF of the front belt 84 between the front distal edge 88 and the front proximal edge 90 (FIGS. 1-3). In such embodiment, when the wearable article is assembled to form the waist opening and the leg openings, the wearable article 20 is folded along the transverse centerline T1 such that the front distal edge 88 is aligned with the back distal edge 88. The front side edge 89 is also aligned with a portion of the back side edge 89. Then the front belt 84 and the back belt 86 are joined at the front and back side edges 89 at the seams 32. The front and back proximal edges 90, however, may not be aligned to one another. The back proximal edge 90 may be disposed longitudinally closer than the front proximal edge 90 relative to the transverse center line T1 such that the proximal portion of the back side panel 82 extends toward the crotch panel 56 of the main body 38 beyond the front proximal edge 90. The side edge of the proximal portion of the back side panel 82 may not be joined to anywhere and free from attachment. Thus, the proximal portion of the back side panel 82 provides a buttock cover 95 as in FIG. 1.

Whether or not the longitudinal length LB of the back belt 86 and the longitudinal length LF of the front belt 84 are the same, the entirety of the longitudinal length LF of the belt side edge 89 of the front belt 84 is seamed with the belt side edge 89 of the back belt 86 to define a seam length LS. When the front belt 84 has straight distal edges 88 and proximal edges 90 that are substantially parallel of each other, then the longitudinal length LF of the front belt 84 is equal to the seam length LS.

The outer sheet 92 of the front or back belt 84, 86 towards the distal edge 88 may be longer than the size of the inner sheet 94 in the longitudinal direction, and an end flap of the outer sheet 92 may be folded over the distal end of the inner sheet 94 at the waist opening. The front and back belts 84, 86 may be provided in low caliper non-woven material for sake of breathability and softness of the belt 40.

The article of the present invention may have good Belt Utilization. What is meant by Belt Utilization is the percentage of dimension of the Full Circumference (mm) compared to the Material Circumference (mm), namely, how effectively the elastic belt is utilized when the wearer or caregiver stretch opens the article for wear, compared to the material used for the belt in the direction of stretch. The Material Circumference is meant to measure the original dimension of the belt sheet material prior to being processed for making the article. The Full Circumference is meant to measure the maximum circumference to which the article may be stretch opened. The article of the present invention has a Belt Utilization of at least 92%. The article of the present invention may have a Full Circumference of from about 610 mm to about 670 mm for Size 3 (or M size, for wearers of body weight 6-11 kgs), or from about 660 mm to about 720 mm for Size 4 (or L size, for wearers of body weight 9-14 kgs), or from about 710 mm to about 760 mm for Size 5 (or XL size, for wearers of body weight 12-17 kgs).

The article of the present invention may have a suitable Fit Circumference Force (N). What is meant by Fit Circumference Force is the unloading force at a certain stretch level which is believed to simulate the force felt by the wearer while wearing the article. The level of stretch which is believed to be felt by the wearer while wearing the article is represented by the 70% Stretch Circumference. The article of the present invention has a Fit Circumference Force of no less than 2.0N. By having such Fit Circumference Force, the elastic belt provides good fit to prevent sagging and leakage.

The article of the present invention may have a suitable Stretch Circumference Force (N). What is meant by Stretch Circumference Force is the loading force at a certain stretch level which is believed to simulate initial stretch experience felt by the wearer or caregiver when inserting hands and stretch opening the article. The level of stretch which is believed to be felt by the wearer or caregiver when stretch opening the article is also represented by the 70% Stretch Circumference. The article of the present invention has a Stretch Circumference Force of no greater than 6.0N, or no greater than 5.5N, or no greater than 5.0N. By having such Stretch Circumference Force, the elastic belt can be easily opened and applied.

The Material Circumference (mm), Full Circumference (mm), 70% Stretch Circumference (mm), Fit Circumference Force (N), and Stretch Circumference Force (N), are obtained according to the "Material Circumference Measurement" and "Whole Article Force Measurement" below.

The tensile stress (N/m) of the front and back elastic belts 84, 86, respectively, may be profiled in order to provide the benefits of the present invention. When the front and back belts form a ring like elastic belt wherein all of the elastic bodies sandwiched between the inner sheet and the outer sheet may run in the transverse direction substantially parallel to each other, the tensile stress may be measured, for example, by the Belt Zone Tensile Stress Measurement described herein below. When the elasticity of the front and back elastic belts 84, 86 are provided by a plurality of elastic bodies 96 running in the transverse direction, the tensile stress may be adjusted by one or more of the following methods; 1) elongation rate of the elastic body 96; 2) density (dtex) of the elastic body 96; 3) longitudinal interval of multiple elastic bodies 96; and 4) effective length of elasticity of the elastic body 96 in the transverse direction. By elongation, "0% elongation" is meant the original length of the elastic body. When a portion of an elastic body is removed of its elasticity, the remainder of the intact elastic body capable of imparting elasticity is defined as the "effective length of elasticity of an elastic body". The elastic bodies 96 disposed on the front and/or back belt 84, 86 may be treated such that certain of the area overlapping the front and/or back waist panels 52, 54 of the main body 38 are removed of elasticity. Removal of elasticity from at least a portion of the area overlapping the front and/or back waist panel 52, 54 of at least one elastic body may be advantageous when the main body 38 comprises an absorbent core 62, in that elasticity in the front and/or back area may cause bunching of the absorbent core 62 and interfere with close fit of the main body 38 to the wearer. In one embodiment, at least a portion of, or at least 10% of, or at least 20% of, or at least 30% of, the elasticity of; at least one of, or at least half of, or at least two thirds of, or all of, the elastic bodies are removed in the region overlapping with the front and back waist panels 52, 54 or the absorbent core 62 of the main body 38.

Referring to FIG. 3, the front and back belts 84, 86 are each divided into 4 zones extending in the transverse direction and defined of its position from the distal edge 88 to the proximal edge 90 relative to the percentage of the seam length LS. The entirety of the length of the belt side edge 89 of the front belt 84 is seamed with a certain length of the belt side edge 89 of the back belt 86 to define a seam length LS. When seam length LS is considered 0% at the distal edge 88 and 100% at the proximal edge 90 of the front belt 84, the zones are defined as such: 0-25% is the waist zone 102, 25-50% is the distal tummy zone 104, 50-85% is the proximal tummy zone 106, and 85-100% is the leg zone 108. When there is an elastic body disposed at 25% from the distal edge 88, such elastic body is considered to be included in the waist zone 102. When there is an elastic body disposed at 50% from the distal edge 88, or 85% from the distal edge 88, such elastic body is considered to be included in the proximal tummy zone 106. For embodiments where the back belt 86 has a greater longitudinal length LB than the longitudinal length LF of the front belt 84, the remaining length of "LB minus LS" of the back belt 86 is not counted in the 4 zones described above.

In the article of the present invention, the tensile stress of the front proximal tummy zone 106 may be higher than the tensile stress of any other zone, either in the front or the back. The tensile stress of the front proximal tummy zone 106 may be no less than 200% of the tensile stress of the front distal tummy zone 104. In one embodiment, the tensile stress of the front distal tummy zone 104 may be lower than, or no more than 70% of, the tensile stress of the back distal tummy zone 104. In one embodiment, the tensile stress of the front proximal tummy zone 106 may be no less than 150% of the tensile stress of the back proximal tummy zone 106. Without being bound by theory, such profiling of the tensile stress per zone is believed to provide the article of the present invention with a shaped elastic belt 40 that conforms well to a human body, particularly to a lower torso of a child of less than 36 months of age, and therefore provide good fit and comfort to the wearer, without compromise of sagging prevention or leakage prevention. Namely, the front proximal tummy zone 106 is subject to high tensile stress such that the article may be anchored against the wearer's trochanter, while leaving more area for the back proximal tummy zone 106 to accommodate the wearer's buttock. As long as the article is anchored securely at the trochanter, the leg zone 108 adjacent the leg opening may be provided with significantly less tensile stress compared to the proximal tummy zone 106. Thus, the soft fit at the front leg opening region 120 facilitates leg movement. Further, by providing a higher tensile stress to the back distal tummy zone 104 compared to the front distal tummy zone 104, the wearer's front waist area is accommodated.

Figure 4:
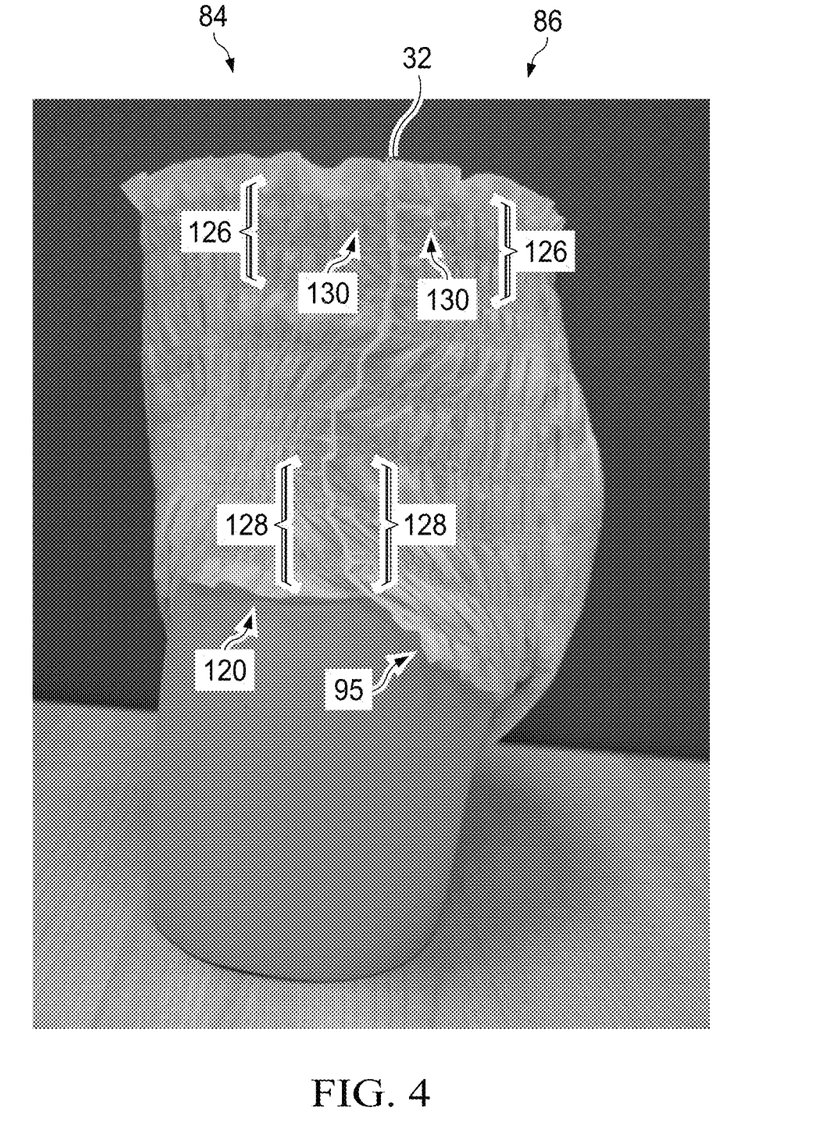
FIG. 4 is a side view of one embodiment of a wearable article of the present invention worn on a mannequin.

As a result of the profiling as described above, the article of the present invention may take an S-curve side seam 32 observed by the side when worn by the wearer, as shown as in FIG. 4. In that the front belt 84 is pulled toward the front side due to the highest tensile stress in the article of the front proximal tummy zone 106, the remainder of the side seam 32 may be curved accordingly. When the waist belt 40 of the present invention is measured against the Belt Seam Shape Measurement method described hereinbelow, the d value may be no less than +10 mm, or no less than +15 mm, or no less than +20 mm. Such d value is indicative of the article conforming to the relatively greater front waist area and buttock area of the wearer, while providing good anchoring at the front proximal tummy zone 106. The curved side seam 32 and positive d value is observed no matter how the stretch board 180 is inserted in the sample, so long as a certain amount of time is allowed for the sample to reach equilibrium. Such behavior of the waist belt 40 of the present invention is in contrast with many belt-type wearable articles available in the market, wherein the side seam takes a relatively straight line, or a line slightly slanted toward the back. For such articles available in the market, the d value according to the Belt Seam Shape Measurement herein may be negative. The tensile stress of the front leg zone 108 may be from 80% to 200% of the tensile stress of the back leg zone 108. In one embodiment, the tensile stress of the front waist zone 102 may be from 80% to 120% of the tensile stress of the back waist zone 102.

The article of the present invention may have a plurality of elastic bodies disposed on each of the zones for providing the tensile stress. The elastic bodies disposed on the front proximal tummy zone 106 may have a density of no less than 540 dtex. The elastic bodies on the front proximal tummy zone 106 may be disposed at an elongation of from 150% to 250%. In one embodiment, from 6 to 18 elastic bodies may be disposed on the front proximal tummy zone 106.

In the present invention, at least some, or at least 3, of the elastic bodies in the front waist zone 102 and those in the back waist zone 102 may be so configured to more or less match locations at the side seam 32. In one embodiment, at least some, or at least 3 of the elastic bodies in the front leg zone 108 and those in the back leg zone 108 may be so configured to more or less match locations at the side seam 32. The front and back waist zones 102 may be disposed of 3 or 4 elastic strands closest to the waist opening and matching at the side seam 32, such that the gathers created by the elastic strands provide a waist band appearance 126 as shown in FIG. 4. The front and back leg zones 108 may be disposed of 3 or 4 elastic strands closest to the front leg opening region 120 and matching at the side seam 32, such that the gathers created by the elastic strands provide a leg band appearance 128 as shown in FIG. 4. The waist and leg band appearances 126, 128, may connote good fit or leakage prevention to the wearer or caregiver.

Still referring to FIG. 4, the waist zone 102 may comprise one interval between elastic bodies of 10-20 mm. Such relatively large interval may provide gathers suitable as a finger hook 130 in which the wearer or caregiver may insert fingers for ease of pulling up the article 20. The gathers for providing a waist band appearance 126 described above may also function as the ergonomically favorable finger hook 130. In the present invention, 2-3 elastic bodies located closest to the waist opening may be disposed with an interval of 2-4 mm to create an array of elastic bodies and matched at the side seam 32, and the interval adjacent such array of elastic bodies may provide a finger hook 130.

The elastic profiling described herein may be utilized for economically making an article of no less than 420 mm, or no less than 450 mm, or no less than 500 mm in the longitudinal axis by using a total of no more than 60, or no more than 46 elastic bodies for the elastic belt 40 per article. The article of the present invention may have an entire longitudinal length of the article of from 350 mm to 600 mm, an effective transverse belt width (LW) of from 315 mm to 500 mm, a back belt longitudinal length (LB) of from 100 mm to 180 mm, a front belt longitudinal length (LF) of from 80 mm to 160 mm, a main body longitudinal length of from 310 mm to 560 mm, and a main body transverse width of from 150 mm to 210 mm. The article of the present invention may have a distance between the distal edge of the front belt to the longitudinal edge of the main body of from 0 mm to 70 mm, and a distance between the distal edge of the back belt to the longitudinal edge of the main body of from 0 mm to 90 mm, and such distances on the front and back belt may be the same or different. The longitudinal length of the main body may be from 70% to 100% of the entire longitudinal length of the article. When the main body comprises an absorbent core 62, the core may have a longitudinal length of from 270 mm to 500 mm, a maximum transverse width of the core of from 90 mm to 125 mm, and a distance between the longitudinal edge of the core to the longitudinal edge of the main body of from 10 mm to 40 mm. The longitudinal length of the core may be from 60% to 95% of the entire longitudinal length of the article, or from 66% to 97% of the main body.

In the present invention, the elongation of the elastic bodies disposed on the front and back of the same zone may be substantially matched. When a certain length of the elastic body is removed of its elasticity, the effective length of elasticity of such elastic body is considered. By matching the elongation rate of the elastic bodies disposed on the front and back of the same zone, and having the front and back belt 84, 86 have the same width LW, the article 20 may be manufactured such that in the unstretched, contracted condition, the article 20 can be flattened. The aforementioned shaping effect of the article 20 conforming to the wearer's body shape is exerted only when the article 20 is in the stretched, wearable condition. Such flattening capability is found for many commercially available pant-type wearable articles, and provides many benefits for providing the article economically. The capability of being flattened accommodates assembling, transferring, and packaging of the article 20.

The obtained wearable article of the present invention may provide ease of application, fit, comfort during wear, prevention of sagging, and prevention of leakage. The obtained wearable article of the present invention may have good Belt Utilization, and thus be made in an economical manner.

Material Circumference Measurement

The sample article is opened at both side seams in a manner such that the front and back belts are peeled away from each other without removing the side seam area, and the portion approximately 30-35 mm from the waist opening is cut along the transverse direction for both the front side and back side of the article. In order to remove the elasticity from the elastic bodies attached to the belt sheets of either the front or back belt, medical cold spray, such as La Pointique Int'l Ltd. Cold spray 829, is applied. The front and back belts are stretched by hand immediately after the cold spray is applied to detach the elastic bodies from the belt sheets, such that the elasticity is loosened completely. If any gathers caused by the elastic bodies are remained, further apply the cold spray at the part where gathers exist and stretch again until gathers are removed. If there are any main body elements remaining on the front and back belts such as core, backsheet or topsheet, then main body elements are also removed. For each sample article, 2 specimens are prepared utilizing the front belt and the back belt, respectively.

For each specimen thus prepared above, the side seam area is identified, and is hung on a stand wherein only the side seam area is clamped using a 40 mm-wide fixed clip positioned 400-500 mm from the measurement table, such that the transverse direction of the specimen matches the vertical direction. The lower end of the specimen is attached to a 40 mm-wide movable clip, also such that only the side seam area is clamped, with an appropriate weight to make a total of 200 g, which thus applies a 200 gf tension to the specimen. Measure the distance of the inside of one side seam area to the other inside of the other side seam area of the specimen by a generic metal ruler to the nearest 1 mm. Separately, measure the transverse width of the side seam area by a generic metal ruler to the nearest 1 mm.

The sum of: the length of the inside of the side seam areas for the front belt specimen, the left and right side seam area width of the front belt specimen, the length of the inside of the side seam areas for the back belt specimen, and the left and right side seam area width of the back belt specimen; thus obtained above is defined as the Material Circumference (mm). Each sample is measured 3 times respectively, and the average is obtained.

Whole Article Force Measurement

Force is measured using an Electronic Tensile Tester with a computer interface such as the MTS Criterion C42 running TestWorks 4 Software (available from MTS SYSTEMS (CHINA) CO., LTD) or equivalent instrument. A load cell is selected so that force results for the samples tested will be between 10 and 90% of capacity of the load cell used. The instrument is calibrated according to the manufacturer's instructions. All testing is performed in a room maintained at 23±2° C. and 50±5% relative humidity.

Figure 5:
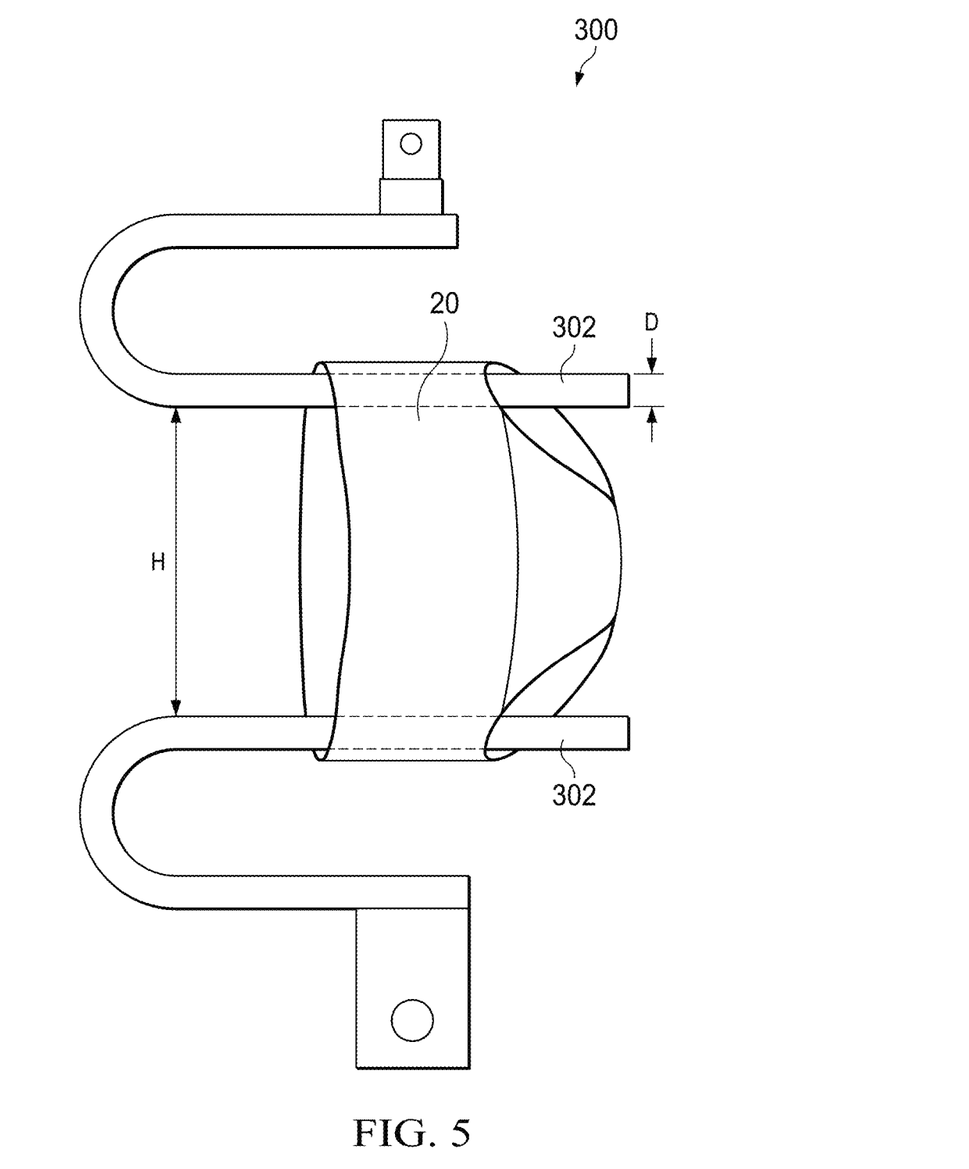
FIG. 5 is a schematic view of an example of a hanger-type sample holding fixture according to the "Whole Article Force Measurement".

The tensile tester is fitted with hanger-type sample holding fixtures 300 as shown in FIG. 5. Each fixture comprises a rigid linear rubber-coated horizontal bar section 302 to prevent sample slippage during testing. The outer bar diameter (including the rubber coating) of the horizontal bar sections is 10.0 mm. The central axes of the horizontal bar sections 302 are configured to remain parallel and in the same vertical plane throughout the test procedure. The gauge circumference is determined by the following equation:

$$\text{Gauge Circumference} = 2 \times (H + D + \pi D/2)$$

where $H$ is the vertical gap between the horizontal bar sections 302, and $D$ is the outer diameter of the bar.

The instrument is set up to go through the following steps:

| | |
|---|---|
| Crosshead Speed | 254.0 mm/min |
| Final Load Point | 19.6 N |
| Hold Time | 0 |
| Number of Cycles | 1 |
| Data Acquisition Rate | 50 Hz |

A sample article 20 is inserted onto the upper horizontal bar section 302 so that the bar passes through the waist opening and one leg opening of the article. The crosshead is raised until the specimen hangs above the lower bar and does not touch lower bar 302. The load cell is tared and the crosshead is lowered to enable the lower bar 302 to be inserted through the waist opening and other leg opening without stretching the article. The article is adjusted so that the longitudinal centerline L1 of the article is in a horizontal plane halfway between the upper and lower bars 302. The center of the side portion in contact with the bar 302 is situated on the same vertical axis as the instrument load cell. The crosshead is raised slowly while the article is held in place by hand as necessary until the force is between 0.05 and 0.1N, while taking care not to add any unnecessary force. The gauge circumference at this point is the Initial Gauge Circumference. The test is initiated and the crosshead moves up at 254 mm/min until a force of 19.6N is attained, then the crosshead immediately returns to the Initial Gauge Circumference at the same speed. The maximum circumference at 19.6N and the force at 70% stretch circumference during the extension segment of the test are recorded.

The maximum circumference at 19.6N is defined as the Full Circumference (mm). The 70% Stretch Circumference (mm) is defined as the Full Circumference×0.70. The Stretch Circumference Force is defined as the force at 70% Stretch Circumference during the load (extension) segment of the test. The Fit Circumference Force is defined as the force at 70% Stretch Circumference during the unload (contraction) segment of the test.

Five samples are analyzed and their average Initial Gauge Circumference, average Full Circumference, average Stretch Circumference Force and average Fit Circumference Force are calculated and reported to the nearest 1 mm or 0.01 N, respectively.

Zone Tensile Stress Measurement

The Zone Tensile Stress Measurement herein is for articles wherein the front belt and the back belt form a ring-like elastic belt, and all of the elastic bodies sandwiched between the inner sheet and the outer sheet run in the transverse direction substantially parallel to each other.

The tensile stress (N/m) is calculated by tensile force (N) divided by the longitudinal length (m) of the specimen. Force may be measured using an Electronic Tensile Tester with a computer interface such as the MTS Criterion C42 running TestWorks 4 Software (available from MTS SYSTEMS (CHINA) CO., LTD) or equivalent instrument. A load cell is chosen so that force results for the samples tested will be between 10 and 90% of capacity of the load cell. The instrument is calibrated according to the manufacturer's instructions. All testing is performed in a room maintained at 23±2° C. and 50±5% relative humidity. The instrument is equipped with single line contact grips at least as wide as the test specimen.

To obtain test specimens, the sample article is opened at both side seams in a manner such that the front and back belts are peeled away from each other without removing the side seam area, and the front and rear elastic belts are removed from the main body 38 by separating the bonding between the waist belt and main body. Cold spray may be used, paying attention not to make wrinkles in the belt sections. Care is taken not to spray on any belt elastic body 96. The obtained elastic belts 40 are severed into zones 102, 104, 106, 108 as defined above with care not to cut any elastic body 96. Samples are pre-conditioned at 23±2 C.° and 50±5% relative humidity for two hours prior to testing. Measure the longitudinal length of each specimen by a generic metal ruler to the nearest 1 mm. By longitudinal length, what is meant is the dimension 102, 104, 106, or 108 in FIG. 3.

The instrument is set up to go through the following steps. Initial Gauge Length is calculated from the Initial Gauge Circumference which is determined during the Whole Article Force Test using separate identical articles, as described above. The Initial Gauge Length is defined as 50% of the Initial Gauge Circumference. The Final Gauge Length is calculated from the Full Circumference which is determined during the Whole Article Force Test, as described above.

| | |
|---|---|
| Crosshead Speed | 254.0 mm/min |
| Data Acquisition Rate | 50 Hz |
| Final Gauge Length | 0.5 × Full Circumference |
| Hold Time | 0 |
| Number of Cycles | 1 |

One end of the specimen is clamped into the upper clamp using the side seam area and the load is tared. The other end of the specimen is clamped into the lower clamp also using the side seam area, such that only the side seam areas are behind the contact line of the grip. The test is started and the specimen is extended to the Final Gauge Length at a crosshead speed of 254 mm/min, then immediately returned to the Initial Gauge Length at the same speed. The specimen is extended in the article transverse direction during the test. The unload force at 70% of the Final Gauge Length during the unload segments of the test is recorded.

Five articles are analyzed and the unload forces are recorded for each of the front and back zones 102, 104, 106, 108. The average tensile force (N) is calculated to the nearest 0.01 N for each zone including the front and back specimens for that zone. The tensile stress for each zone is calculated by the average tensile force (N) divided by the average longitudinal length (m) and reported to the nearest 0.1 N/m.

Belt Seam Shape Measurement

The Belt Seam Shape Measurement herein is for articles wherein the front belt and the back belt form a ring-like elastic belt, and all of the elastic bodies sandwiched between the inner sheet and the outer sheet run in the transverse direction substantially parallel to each other.

A belt specimen from the sample article and a board (hereinafter "stretch board") for supporting the specimen according to the size of the specimen are prepared.

The belt specimen is prepared by removing the waist belt 40 from the main body 38 of the article by separating the bonding between the waist belt and main body. Cold spray may be used, paying attention not to make wrinkles in the belt sections. Care is taken not to spray on any belt elastic body 96. The seam length LS (see FIG. 2, for example, wherein LS equals LF) of the sample is measured to within ±1 mm with the belt laid flat and no tension applied.

The Full Circumference is determined during the Whole Article Force Test using separate identical articles as described above. The Full Stretch Width is defined as 50% of the Full Circumference.

Figure 6:
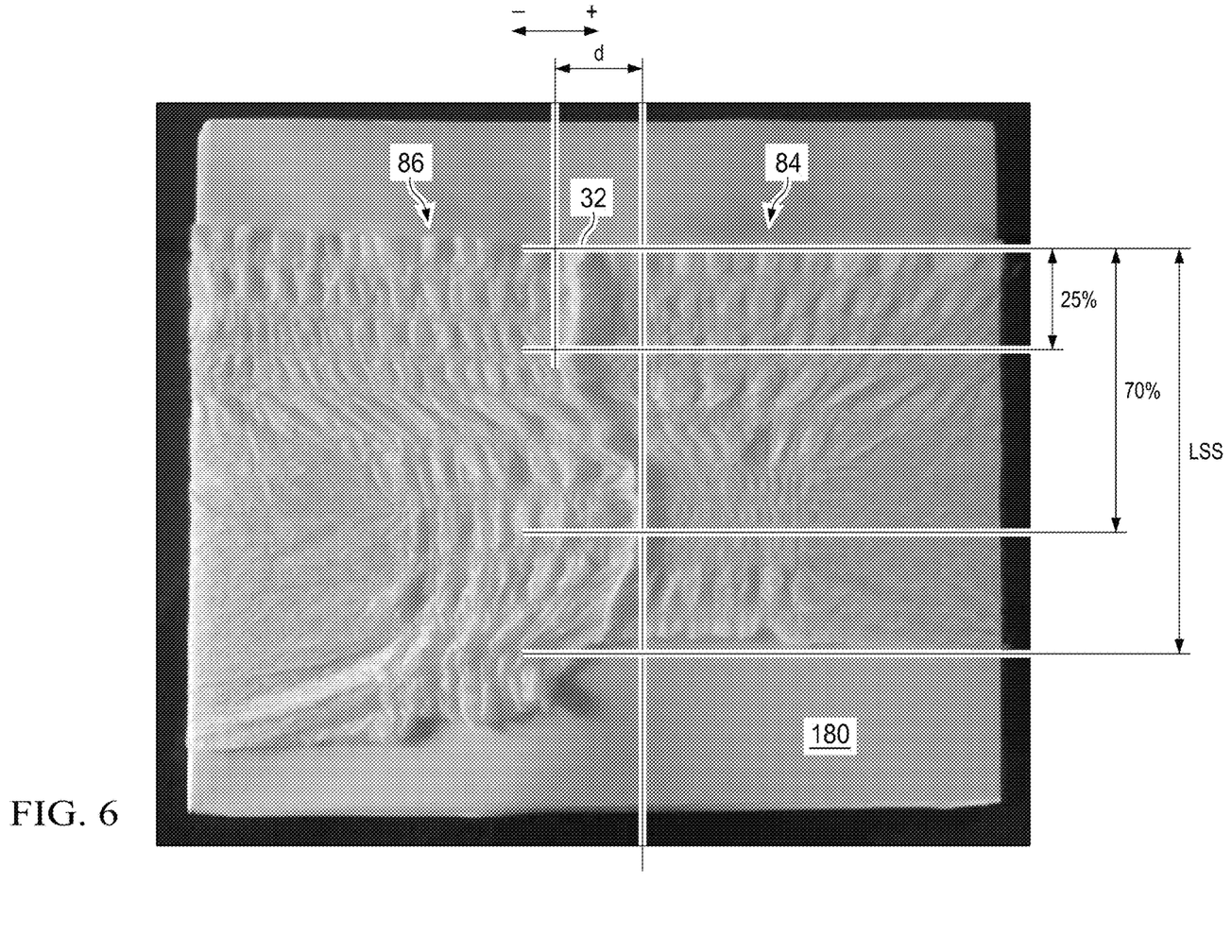
FIG. 6 is a side view of one embodiment of a wearable article of the present invention worn on a stretch board according to the "Belt Seam Shape Measurement".

Referring to FIG. 6, the stretch board 180 is made of polymethyl methacrylate, polycarbonate, or similar rigid material and has a dimension as such:

| | |
|---|---|
| Thickness | 8.5 mm ± 5 mm |
| Length | Between [the seam length (LS) + 40 mm] to [the seam length (LS) + 100 mm] |
| Width | 70% of the Full Stretch Width of the sample specimen − board thickness |

For example, if the belt side seam length LS is 130 mm, the stretch board length should be 170-230 mm. If the Full Stretch Width of the specimen is 355 mm and the board thickness is 8.5 mm, the board width should be 240 mm.

The stretch board 180 is inserted in the specimen while stretching the specimen as little as possible to insert the board, and in a manner such that the entire length of the seams 32 are placed on the front and back planes (and not on the sides) of the stretch board 180, such as shown in FIG. 6. The specimen is adjusted on the stretch board 180 so that the distal edge 88 (i.e. at the waist opening) of each seam 32 on one side and the other of the stretch board 180, as well as the proximal edge (i.e. at the leg opening) of each seam 32 on one side and the other of the stretch board 180 are aligned to within ±5 mm, respectively, of the same longitudinal axis.

The specimen with the stretch board 180 inserted is then stood for 1 min to reach equilibrium in an environment at 25±2° C. and 50±10% relative humidity. Referring to FIG. 6, the linear end-to-end side seam length (rather than the contour length) in this stretched condition (LSS) is measured. The positions of the seam 32 in the transverse direction at points 70% of LSS away from the waist opening (70% point) and at 25% of LSS away from the waist opening (25% point) in the longitudinal direction are measured, and the difference "d" (unit: mm) is obtained. The value d is positive when the 70% point is located closer to the front longitudinal centerline of the belt compared to the 25% point. The value d is negative when the 25% point is located closer to the front longitudinal centerline of the belt compared to the 70% point. The d value is obtained for both seams 32 on either side of the stretch board 180. The "d" values are measured for five samples and the average d value (average of 10 values) is reported to the nearest 1 mm.

EXAMPLES

Example 1

A wearable article of the present invention having an elastic profiling according to FIGS. 2, 3, and Table 1 below having a seam length LS of 130 mm.

Comparative Example 1

A wearable article of the prior art having an elastic profiling according to FIGS. 2, 3, and Table 1 below also having a seam length LS of 130 mm.

Comparative Example 2

A wearable article purchased online from Beijing, PRC on October 2015 having a tradename of "Huggies Silver Pants L size" having Lot No. ND31 C manufactured on Aug. 15, 2015.

Comparative Example 3

A wearable article purchased online from Beijing, PRC on October 2015 having a tradename of "Merries Pants L size" having Lot No. EOC12495 manufactured on Sep. 6, 2015.

Elastic bodies indicated as "tummy cut" are removed of elasticity at the central area of the central panels 80 overlapping with the main body 38, and have 66% effective length of elasticity.

The Belt Utilization, Fit Circumference Force, and Stretch Circumference Force for Example 1 and Comparative Examples 1-3 were measured according to the Material Circumference Measurement and Whole Article Force Measurement method herein, and results are shown below in Table 2.

TABLE 2

|  | Example 1 | Comparative Example 1 | Comparative Example 2 | Comparative Example 3 |
| --- | --- | --- | --- | --- |
| Material Circumference (mm) | 733 | 733 | 744 | 741 |
| Full Circumference (mm) | 677 | 614 | 666 | 673 |
| Belt Utilization (%) | 92% | 84% | 90% | 91% |
| Fit Circumference Force (N) | 2.5 | 3.5 | 3.1 | 3.5 |
| Stretch Circumference Force (N) | 5.3 | 9.4 | 6.3 | 6.8 |

For Example 1, the tensile stress for each zone were measured according to the Zone Tensile Stress Force Measurement, and the value d was measured according to the Belt Seam Shape Measurement methods herein. For Example 1, the tensile stress of the front proximal tummy zone is highest among any other zone, and is more than 200% of the tensile stress of the front distal tummy zone 104, and is more than 150% of the tensile stress of the back proximal zone. Also for Example 1, the tensile stress of the front waist zone 102 was between 80-120% of the tensile stress of the back waist zone 102, and the tensile stress of the front leg zone 108 was between 80-200% of the tensile forces stress of the back leg zone 108. Example 1 provided a d-value of over +20 mm.

Consumer Acceptance

Example 1 and Comparative Example 1 including an identical absorbent core, as well as Comparative Examples 2 and 3 were subjected to a consumer test for application on 15 panelists each. The panelists were caregivers of Chinese Size 4 (L-size) wearers of age 6-31 months, weighing 9-14 kgs. There were 7 boys and 8 girls as wearers.

The wearers were applied the Example articles, and the panelists were asked to rate Questions 1 through 4 in Table 3. Then, the articles were loaded with 150 ml of saline solution, and the wearers were allowed to spontaneously

TABLE 1

| | dtex/elongation %/number of elastic bodies | |
| --- | --- | --- |
| | Example 1 | Comparative Example 1 |
| Front waist zone | 540dtex/150%/4 | 540dtex/170%/4 |
| Front distal tummy zone | 540dtex/150%/2 | 540dtex/170%/2 |
| | 540dtex/150%/2 with tummy cut | 540dtex/275%/2 with tummy cut |
| Front proximal tummy zone | 940dtex/210%/8 with tummy cut | 540dtex/275%/2 with tummy cut |
| | | 940dtex/275%/6 with tummy cut |
| Front leg zone | 540dtex/150%/2 with tummy cut | 540dtex/275%/2 with tummy cut |
| Back waist zone | 540dtex/150%/4 | 540dtex/170%/4 |
| Back distal tummy zone | 940dtex/130%/4 | 940dtex/170%/4 |
| Back proximal tummy zone | 540dtex/210%/6 with tummy cut | 540dtex/275%/6 with tummy cut |
| Back leg zone | 540dtex/210%/2 with tummy cut | 540dtex/275%/2 with tummy cut | play, walk, crawl or run for 15 minutes while the article or wearer was not touched. After the 15 minute activity, the panelists were asked to rate Question 5 in Table 3.

Except for Question 2, the panelists were asked to rate the performance in 5 scales from "Very Poor" to "Excellent", wherein 5 represents "Excellent", 4 represents "Good", 3 represent "Fair", 2 represent "Poor" and 1 represents "Very Poor". For Question 2, the panelists were asked to rate belt tightness as such: 2 represents "too tight", 1 represents "tight", 0 represents "just right", −1 represents "loose", and −2 represents "too loose". The ratings were averaged and statistically analyzed. Test results are shown below in Table 3.

TABLE 3

| Question | Example 1 | Comparative Example 1 | Comparative Example 2 | Comparative Example 3 |
|---|---|---|---|---|
| 1 Belt Tightness Overall Rating | 4.1 | 2.6 | 3.5 | 4.2 |
| 2 Just right belt tightness | −0.14(*1) | 0.78 | −0.28 | 0.14 |
| 3 Easy application | 4.7 | 3.7 | 4.5 | 4.5 |
| 4 Initial Overall fit | 4.5(*2) | 3.6 | 3.6 | 4.6 |
| 5 Overall sagging performance rating after activity | 3.4 | 3.4 | 2.6 | 4.1 |

(*1)statistically significantly better than Comparative Example 1 with 90% confidence
(*2)statistically significantly better than Comparative Example 1 and Comparative Example 2 with 90% confidence As can be seen from these results, although the Belt Utilization of Example 1 is higher than Comparative Examples 1-3, the consumer perception of the tightness and fit (Questions 2 and 4) of Example 1 is significantly better than Comparative Example 1, better than Comparative Example 2, and about the same as Comparative Example 3. Further, despite Example 1 had significantly better fit performance (Question 4) than Comparative Example 2, it also had better sagging prevention (Question 5) than Comparative Example 2.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A wearable article comprising a main body and an elastic belt comprising a front belt and a back belt, the main body being continuous with the front belt and the back belt, and transverse edges of the front belt and the back belt are joined to form laterally opposed side seams such that a waist opening and two leg openings are formed;
    wherein each of the front belt and back belt are formed by an inner sheet, an outer sheet, and a plurality of elastic bodies sandwiched therebetween;
    wherein at least some of the elastic bodies run in a transverse direction substantially parallel to each other;
    wherein, as measured according to a Material Circumference Measurement and a Whole Article Force Measurement as set forth herein, a Belt Utilization is 92%, and a Fit Circumference Force is greater than 2.0N;
    wherein an entire length of each of the transverse edges of the front belt is seamed with less than an entire length of a corresponding one of the transverse edges of the back belt to define a seam length LS that is the same for each seam;
    wherein the front and back belts are each divided into four zones extending in the transverse direction and each zone being defined by its location from a distal edge to a proximal edge relative to the percentage of the seam length LS wherein: 0-25% is a waist zone, 25-50% is a distal tummy zone, 50-85% is a proximal tummy zone, and 85-100% is a leg zone; and
    wherein a tensile stress of the front proximal tummy zone is higher than a tensile stress of any other zone, and no less than 200% of a tensile stress of the front distal tummy zone.

2. The article of claim 1, wherein a Stretch Circumference Force according to the Whole Article Force Measurement is no greater than 6.0N.

3. The article of claim 1, wherein a Full Circumference according to the Whole Article Force Measurement is no less than 660 mm.

4. The article of claim 1, wherein the front belt and the back belt form a ring-like elastic belt, wherein a center portion of the front belt is joined to a front waist panel of the main body, and a center portion of the back belt is joined to a back waist panel of the main body, wherein the front and back belts each have a left side panel and a right side panel where the main body does not overlap, wherein all of the elastic bodies sandwiched between the inner sheet and the outer sheets of the front and back belts run in the transverse direction substantially parallel to each other.

5. The article of claim 1, wherein each of the elastic bodies disposed in the front proximal tummy zone are disposed at an elongation of from 150% to 250%.

6. The article of claim 1, wherein each of the elastic bodies disposed in the front proximal tummy zone has a density of no less than 540 dtex.

7. The article of claim 1, wherein a tensile stress of the front distal tummy zone is lower than a tensile stress of the back distal tummy zone.

8. The article of claim 7, wherein the tensile stress of the front distal tummy zone is no more than 70% of the tensile stress of the back distal tummy zone.

9. The article of claim 1, wherein the tensile stress of the front proximal tummy zone is no less than 150% of the tensile stress of the back proximal tummy zone.

10. The article of claim 1, wherein a tensile stress of the front leg zone is from 80% to 200% of a tensile stress of the back leg zone.

11. The article of claim 1, wherein a tensile stress of the front waist zone is from 80% to 120% of a tensile stress of the back waist zone.

12. The article of claim 1, wherein a d value as measured according to a Belt Seam Shape Measurement as set forth herein is no less than +10 mm.

13. The article of claim 1, wherein the main body comprises an absorbent core and wherein the plurality of elastic bodies of the front and back belts do not overlap the absorbent core.

14. The article of claim 1, wherein the plurality of elastic bodies of the front belt substantially meet the plurality of elastic bodies of the back belt at the transverse edges of the front and back belts at the side seams in the waist zones.

15. The article of claim 14, wherein the plurality of elastic bodies of the front belt do not meet the plurality of elastic bodies of the back belt at the transverse edges of the front and back belts at the side seams in the distal tummy zones.

16. The article of claim 1, wherein the plurality of elastic bodies of the front belt do not meet the plurality of elastic bodies of the back belt at the transverse edges of the front and back belts at the side seams in the proximal tummy zones.

17. The article of claim 16, wherein the plurality of elastic bodies of the front belt do not meet the plurality of elastic bodies of the back belt at the transverse edges of the front and back belts at the side seams in the leg zones.

18. The article of claim 1, wherein portions of the transverse edges of the back belt that are not seamed with the transverse edges of the front belt form a buttocks cover region, wherein the buttocks cover region comprises at least two elastic bodies.

* * * * *